United States Patent [19]

Brittain et al.

[11] Patent Number: 4,490,381
[45] Date of Patent: Dec. 25, 1984

[54] 1'-SUBSTITUTED SPIRO[MIDAZOLIDINE-4,3'-INDOLINE]2,2',5-TRIONES

[75] Inventors: David R. Brittain, Macclesfield; Robin Wood, Hyde, both of England

[73] Assignee: Imperial Chemical Industries PLC, London, England

[21] Appl. No.: 201,973

[22] Filed: Oct. 29, 1980

[30] Foreign Application Priority Data

Nov. 13, 1979 [GB] United Kingdom ............ 7939235
Aug. 13, 1980 [GB] United Kingdom ............ 8026459
Sep. 15, 1980 [GB] United Kingdom ............ 8029760

[51] Int. Cl.³ .................................... C07D 403/02
[52] U.S. Cl. ............................. 424/273 R; 548/309
[58] Field of Search ............ 548/309; 424/273 R; 542/401

[56] References Cited

U.S. PATENT DOCUMENTS 4,248,882 2/1981 Sarges et al. ................ 548/309

FOREIGN PATENT DOCUMENTS 137976 11/1975 Japan ........................... 548/309

OTHER PUBLICATIONS

Otomasu et al., Chem. Pharm. Bull. 23 (7) 1431-1435, 1975.
Schäfer, Archiv der Pharmazie, 1970, 303, 183-191.
European patent application publication No. 11426.

Primary Examiner—Jane T. Fan
Attorney, Agent, or Firm—Cushman, Darby & Cushman

[57] ABSTRACT

The invention concerns novel 1'-substituted spiro[imidazolidine-4,3'-indoline]-2,2',5-triones of the formula:

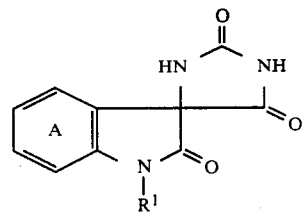

in which $R^1$ is (1–12C)alkyl; phenyl, naphthylmethyl or cinnamyl optionally bearing 1-2 halogeno substituents; or benzyl optionally bearing 1-3 substituents independently selected from halogeno, trifluoromethyl, (1–4C)alkyl, (1–4C)alkoxy, nitro, cyano and hydroxy; and ring A optionally bears one substituent selected from halogeno, (1–4C)alkyl, (1–4C)alkoxy, nitro and hydroxy, or two substituents independently selected from halogeno (1–4C)alkyl and nitro; or a pharmaceutically acceptable salt thereof; but excluding those compounds wherein $R^1$ is methyl, ethyl, n-propyl or unsubstituted benzyl and benzene ring A is unsubstituted.

The compounds of the invention are potent inhibitors of the enzyme aldose reductase and are of use in the treatment or prophylaxis of certain complications of diabetes or galactosemia. The invention also embraces processes for the manufacture of the novel compounds of formula I, as well as pharmaceutical compositions of such compounds. A representative compound is 1'-(2-fluoro-4-bromobenzyl)-spiro]imidazolidine-4,3'-indoline]-2,2',5-trione.

9 Claims, No Drawings

1'-SUBSTITUTED SPIRO[IMIDAZOLIDINE-4,3'-INDOLINE]2,2',5-TRIONES

This invention concerns novel substituted indoline-2-one derivatives, and more particularly novel 1'-substituted spiro[imidazolidine-4,3'-indoline]-2,2',5-triones, which possess the property of inhibiting the enzyme aldose reductase in vivo. The invention also concerns processes for the manufacture of the said substituted indolin-2-one derivatives, pharmaceutical compositions thereof and a method for use thereof in the treatment or prophylaxis of certain complications of protracted diabetes of galactosemia.

The enzyme aldose reductase is responsible for the catalytic conversion of aldoses, for example glucose and galactose, to the corresponding alditols, for example sorbitol and galactitol respectively. Alditols penetrate cell membranes poorly and, once formed, tend to be removed only by further metabolism. As a consequence, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those complications of protracted diabetes or galactosemia which may be due in part to the accumulation of sorbitol or galactitol respectively. Such complications are, for example, macular oedema, cataract, retinopathy or impaired neural conduction.

It is known that certain spiro-linked hydantoins (spiro-linked imidazolidine-2,5-diones) derived from various bicyclic ketones are inhibitors of the enzyme aldose reductase, for example the compounds of the general formula:

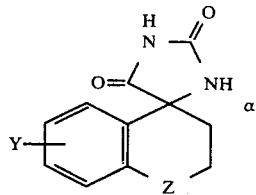

wherein Z is oxygen, sulphur, sulphinyl, sulphonyl, methylene or a direct bond, and Y stands for various optional substituents described by Sarges in U.S. Pat. No. 4,117,230. We have now discovered that certain novel spiro-linked hydantoins of the formula I below and derived from 1-substituted-indoline-2,3-diones possess potent aldose reductase inhibitory properties and this is the basis of our invention. This discovery is surprising in view of the various chemical differences involved, for example in view of the presence of an amidic carbonyl radical in the α-position relative to the spiro-carbon atom, which position is always occupied by a methylene radical in the aldose reductase inhibitory spiro-hydantoins of the prior art. Certain related spiro-hydantoins derived from 1-substituted-indolin-2,3-diones are known. In particular, 1'-methyl-, 1'-allyl- and 1'-benzyl-spiro[imidazolidine-4,3'-indoline]-2,2',5-trione have been described by Otomasu et alia in Chem. Pharm. Bull., 1975, 23, 1431–1435, but no pharmacalogical properties have been ascribed to them.

According to the invention there is provided a 1'-substituted-spiro[imidazolidine-4,3'-indoline]-2,2',5-trione of the formula:

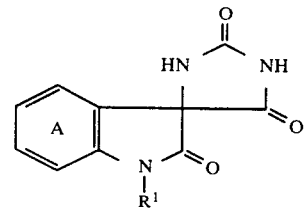

wherein $R^1$ is a (1–12C)alkyl radical, a phenyl, naphthylmethyl or cinnamyl radical the aromatic rings of which optionally bear one or two halogeno radicals, or $R^1$ is a benzyl radical optionally bearing one, two or three substituents independently selected from halogeno, trifluoromethyl, (1–4C)alkyl, (1–4C)alkoxy, nitro, cyano and hydroxy radicals; and benzene ring A optionally bears one substituent selected from halogeno, (1–4C) alkyl, (1–4C)alkoxy, nitro and hydroxy radicals, or bears two substituents independently selected from halogeno, (1–4C)alkyl and nitro radicals; or a pharmaceutically acceptable salt thereof; but excluding those compounds wherein $R^1$ is a methyl, ethyl, n-propyl or unsubstituted benzyl radical, and benzene ring A is unsubstituted.

The compounds of formula I are derivatives of spiro[imidazolidine-4,3'-indoline] which is numbered as follows:

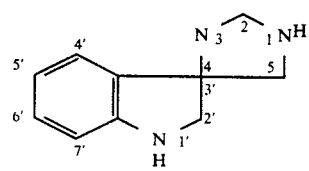

This numbering system will be used throughout the present specification.

The compounds of formula I possess at least one asymmetric carbon atom, namely the spiro-linked carbon atom. They therefore exist, and may be isolated, in racemic and optionally-active forms. This invention relates to the racemic form of a compound of formula I or to any optically-active form which possesses aldose reductase inhibitory properties, it being well known in the art how to prepare optically active forms by resolution of the racemic form, or by synthesis from optically-active starting materials, and how to determine the aldose reductase inhibitory properties by the standard tests described hereinbelow.

A particular value for $R^1$ when it is a (1–12C) alkyl radical is, for example, a methyl, ethyl, propyl, butyl, pentyl, hexyl, nonyl or decyl radical.

Particular values for substituents which may be present on benzene ring A or on an aryl moiety in $R^1$ as defined above are, by way of example only:

for a halogeno, a fluoro, chloro, bromo or iodo radical;

for a (1–4C)alkyl, a methyl or ethyl radical; and for a (1–4C)alkoxy radical, a methoxy or ethoxy radical.

Particular values for ring A are when it is unsubstituted or bears 4'-chloro, 5'-fluoro, 5'chloro, 5'-bromo, 5'-methyl, 5'-methoxy, 5'-hydroxy, 5'-nitro, 6'-chloro, 7'-fluoro, 7'-chloro, 7'-methyl, 7'-ethyl, 5',6'-difluoro, 5',6'-dichloro, 4',5'-dichloro, 5',6'-dimethyl, 5'-bromo-7'-nitro or 5'-chloro-7'-methyl substituents.

Particular values for $R^1$ are when it is a methyl, n-propyl, n-hexyl, n-nonyl, n-decyl, phenyl, cinnamyl, 3,4-dichlorocinnamyl, naphth-1-ylmethyl, naphth-2-ylmethyl, benzyl, 3,4-dichlorobenzyl, 2-fluoro-4-bromobenzyl, 4-methylbenzyl, 2-fluoro-4-iodobenzyl, 3-chloro-4-bromobenzyl, 4-chlorobenzyl, 4-bromobenzyl, 3,4-dimethoxybenzyl, 3-(trifluoromethyl)benzyl, 2-cyanobenzyl, 4-cyanobenzyl, 2-fluoro-4-bromo-5-nitrobenzyl, 4-nitrobenzyl, 3,5-dichloro-4-bromobenzyl, 2,3-dichlorobenzyl, 4-hydroxybenzyl or 3,5-dichlorobenzyl radical.

A preferred value for ring A is when it is unsubstituted or bears a halogeno substituent for example a chloro substituent and especially such a substituent located at position 5', 6' or 7'.

A preferred value for $R^1$ is when it is a benzyl radical bearing one or two halogeno radicals, for example when it is a 4-halogeno-, 2,4-dihalogeno-, 3,4-dihalogeno- or 3,5-dihalogeno-benzyl radical, such as a 4-bromo-, 2-fluoro-4-bromo, 2-fluoro-4-iodo-, 3,4-dichloro-, 3-chloro-4-bromo- or 3,5-dichloro-benzyl radical.

Particular groups of compounds of the invention are comprised by the following compounds of formula I defined hereinbefore wherein:

(a) $R^1$ is a (1–12C)alkyl or an unsubstituted benzyl radical; and benzene ring A bears at least one halogeno substituent;

(b) $R^1$ is a phenyl, cinnamyl or naphthylmethyl radical the aromatic rings of which optionally bear one or two halogeno radicals; and benzene ring A is unsubstituted or bears at least one halogeno substituent; and (c) $R^1$ is a benzyl radical bearing one, two or three substituents independently selected from halogeno, trifluoromethyl, cyano, hydroxy, nitro, methyl and methoxy radicals; and benzene ring A is unsubstituted or bears one or two substituents as defined hereinbefore; and, in each group, together with the pharmaceutically acceptable salts thereof.

One preferred group of compounds of the invention comprises those compounds of formula I wherein $R^1$ and benzene ring A have any of the preferred values specifically defined hereinbefore, together with the pharmaceutically acceptable salts thereof.

A further group of preferred compounds of the invention comprises those compounds of formula I wherein $R^1$ is a 3,4-dichlorobenzyl, 2-fluoro-4-bromobenzyl, 3-chloro-4-bromobenzyl or 2-fluoro-4-iodobenzyl radical and benzene ring A is unsubstituted or bears 5'-fluoro, 5'-chloro, 5'-bromo, 5',6'-difluoro or 5',6'-dichloro substituents; together with the pharmaceutically acceptable salts thereof.

Specific compounds of the invention are mentioned hereinafter in the Examples. However, of these, the following compounds are of special interest:

1'-(3,4-dichlorobenzyl)-spiro[imidazolidine-4,3'-indoline]-2,2',5-trione,

1'-(2-fluoro-4-bromobenzyl)-spiro[imidazolidine-4,3'-indoline]-2,2',5-trione,

1'-(3,4-dichlorobenzyl)-5'-fluorospiro[imidazolidine-4,3'-indoline]-2,2',5-trione, 1'-(3-chloro-4-bromobenzyl)-spiro[imidazolidine-4,3'-indoline]-2,2',5-trione, 1'-(3,4-dichlorobenzyl)-5'-chlorospiro[imidazolidine-4,3'-indoline]-2,2',5-trione, 1'-(2-fluoro-4-bromobenzyl)-5'-chlorospiro[imidazolidine-4,3'-indoline]-2,2',5-trione, 1'-(3,4-dichlorobenzyl)-5'-bromospiro[imidazolidine-4,3'-indoline]-2,2',5-trione, 1'-(2-fluoro-4-bromobenzyl)-5'-fluorospiro[imidazolidine-4,3'-indoline]-2,2',5-trione, 1'-(3,4-dichlorobenzyl)-5',6'-dichlorospiro[imidazolidine-4,3'-indoline]-2,2',5-trione, 1'-(3,4-dichlorobenzyl)-5',6'-difluorospiro[imidazolidine-4,3'-indoline]-2,2',5-trione and 1'-(2-fluoro-4-iodobenzyl)-spiro[imidazolidine-4,3'-indoline]-2,2',5-trione; or a pharmaceutically acceptable salt thereof.

Particular pharmaceutically acceptable salts of formula I are, for example, alkali metal or alkaline earth metal salts, such as sodium, potassium, calcium or magnesium salts, aluminium or ammonium salts, or salts with organic bases, such as triethanolamine, which form pharmaceutically acceptable cations.

The compounds of formula I may be manufactured by any general procedure known in the art to be applicable to the preparation of chemically analogous heterocyclic compounds. Such analogy processes are provided as a further feature of the invention and are illustrated by the following wherein $R^1$ and benzene ring A have the meanings defined hereinbefore:

(a) Reacting an indolin-2,3-dione of the formula:

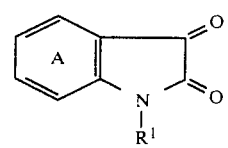

III with an alkali metal cyanide, and ammonium carbonate or carbamate.

A suitable alkali metal cyanide is, for example, sodium or potassium cyanide.

It will be understood that process (a) is an example of the Bucherer-Bergs synthesis of imidazolidine-2,4-diones (hydantoins) which is well known in the art (see E Ware in Chemical Reviews, 1950, 46, 422–425), and that such a reaction may therefore proceed through a hydroxynitrile of the formula:

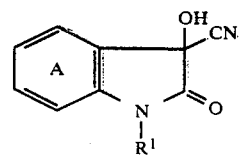

IV and/or an amino-nitrile of the formula:

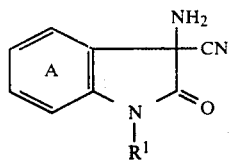

Accordingly, this invention includes carrying out process (a) by separate or in situ manufacture of an intermediate of formula IV (for example by reaction of a compound of formula III with hydrogen cyanide) followed by reaction of the intermediate with ammonium carbonate or carbamate. Similarly, the invention includes carrying out process (a) by separate or in situ manufacture of an intermediate of formula V (for example by reacting a compound of formula III with ammonia and hydrogen cyanide) followed by reaction of the intermediate with carbon dioxide, which may conveniently be provided as ammonium carbonate or carbamate.

The process may be conveniently performed in a solvent or diluent, for example in a (1–4C)alkanol such as methanol or ethanol, or in ethylene glycol or diethylene glycol, preferably containing water, and at a temperature in the range, for example 20°–100° C.

The ammonium carbonate or carbamate may if necessary be formed in situ in conventional manner.

The starting materials of formula III may be obtained by conventional procedures of indole chemistry. For example, those compounds of formula III wherein $R^1$ is other than a phenyl radical may be obtained by reacting an indoline-2,3-dione of formula III wherein $R^1$ is replaced by hydrogen with the appropriate alkyl or aralkyl halide, for example a chloride, bromide or iodide, in the presence of a base such as sodium or potassium hydroxide in dimethyl sulphoxide at a temperature of 20°–40° C.

Those starting materials of formula III wherein $R^1$ is a phenyl radical may be made, for example, by condensation of the appropriate diphenylamine with oxalyl chloride and aluminium chloride, as described in U.S. Pat. Ser. No. 3,509,149.

(b) Reacting a compound of the formula:

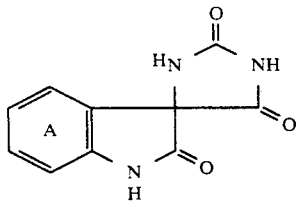

with a compound of the formula $R^2.X$. wherein $R^2$ has the same meaning as $R^1$ other than a phenyl radical and X is a halogeno radical, for example a chloro, bromo or iodo radical, or an aryl or alkylsulphonyloxy radical, for example a toluene p-sulphonyloxy or methylsulphonyloxy radical, in the presence of a suitable base.

It will be appreciated that, in general, it is preferable to use approximately three molecular equivalents of base, and one equivalent of the compound of the formula $R^2.X$.

A particularly suitable base is, for example, a strong base, for example an alkali metal hydroxide, carbonate or hydride, such as sodium or potassium hydroxide or carbonate and sodium or potassium hydride. The process is preferably performed in a solvent or diluent, for example in a (1–4C)alkanol such as methanol or ethanol or in N,N-dimethylformamide, optionally admixed with water, when an alkali metal hydroxide or carbonate is used, or in a non-aqueous solvent, such as dimethyl sulphoxide or N,N-dimethylformamide, when an alkali metal hydride is used.

The process is preferably carried out at a temperature of, for example, 20°–40° C., and generally for a relatively short reaction time to minimise alkylation of the imidazolidine nitrogen atoms.

The starting materials of formula VI may be made by standard procedures of organic chemistry well known for the synthesis of analogous compounds, for example as described by Otomasu et alia (Chem.Pharm. Bull., 1975, 23, 1431–1435). Thus, they may be obtained by an analogous procedure to process (a) hereinabove, but starting from the appropriate 1-(unsubstituted)-indoline-2,3-dione. The latter compounds are also readily accessible by known procedures of organic chemistry.

(c) Reacting a compound of the formula:

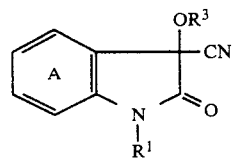

wherein $R^3$ is an acyl or tri-[(1–4C)alkyl]silyl radical with ammonium carbonate or carbamate.

A particular value for $R^3$ when it is an acyl radical is, for example, a (1–6C)alkanoyl radical such as acetyl or propionyl radical, a phenylsulphonyl, toluene p-sulphonyl or benzoyl radical.

A particular value for $R^3$ when it is a tri-[(1–4C)alkyl]silyl radical is, for example a trimethylsilyl radical.

It will be recognised that process (c) is a modification of process (a) hereinbefore and consequently similar reaction conditions may be used. Similarly the ammonium carbonate or carbamate may be formed in situ if desired.

The starting materials of formula VII may be made by conventional procedures. Thus, they may be obtained by reacting a hydroxynitrile of formula IV (itself obtained as described in process (a) by reaction of an indoline-2,3-dione with hydrogen cyanide) with an appropriate acyl or tri-[(1–4C)alkyl]silyl halide, for example acetyl, propionyl, phenylsulphonyl, toluene p-sulphonyl, benzoyl or trimethylsilyl chloride, in conventional manner.

Alternatively, those compounds of formula VII wherein $R^3$ is a tri-[(1–4C)alkyl]silyl radical may be conveniently obtained by reaction of an appropriate indoline-2,3-dione with a tri-[(1–4C)alkyl]silyl cyanide, for example trimethylsilyl cyanide, at a temperature in the range, for example, 15°–40° C. and in a non-aqueous solvent, for example 1,2-dimethoxyethane.

(d) For a compound of formula I wherein benzene ring A bears a nitro substituent and/or $R^1$ is a benzyl radical bearing a nitro substituent, nitrating the corresponding compound of formula I in which benzene ring A and/or the radical $R^1$ bear no more than two substituents.

The nitration may be carried out under conventional procedures, for example in the presence of sulphuric acid, using nitric acid at a temperature in the range, for example, 0° to 30° C., or using fuming nitric acid at a temperature in the range, for example −20° to 10° C.

(e) For a compound of formula I wherein benzene ring A bears a chloro or bromo substituent, chlorinating or brominating the corresponding compound of formula I in which benzene ring A is unsubstituted.

The chlorination or bromination may be carried out using conventional procedures, for example using elemental chlorine or bromine optionally in the presence of a Friedel-Craft's catalyst such as ferric chloride, ferric bromide or iron powder, at a temperature in the range, for example 10° to 100° C. and in a suitable solvent or diluent, for example chloroform, nitrobenzene or acetic acid.

Alternatively, the chlorination or bromination may be carried out using sulphuryl chloride or bromide optionally in the presence of iodine as catalyst at a temperature in the range, for example 10° to 100° C., and in a suitable solvent or diluent, for example acetic acid or chloroform.

(f) For a compound of formula I wherein benzene ring A and/or $R^1$ bears a hydroxy radical, dealkylating the corresponding compound of formula I wherein benzene ring A and/or $R^1$ bears a (1-4C)alkoxy radical.

The dealkylation may be carried out using conventional procedures well known in the art, for example using a mixture of an organic tertiary base, for example pyridine, quinoline or (1-4C)alkyl derivatives thereof, together with a mineral acid, for example hydrochloric or hydrobromic acid, at a temperature in the range for example 80° to 150° C. The organic tertiary base may conveniently be used in excess and function as a solvent or diluent.

Whereafter when a pharmaceutically acceptable salt is required, a compound of formula I is reacted with an appropriate base affording a pharmaceutically acceptable cation, using a conventional procedure.

Further, when an optically active form of a compound of formula I is required, a racemic form of the said compound may be reacted with an optically-active form of a suitable organic base, for example brucine, coniine or 2-pipecoline, followed by conventional separation of the diastereoisomeric mixture of salts thus obtained, for example by fractional crystallisation from a suitable solvent, for example a (1-4C)alkanol, whereafter the optically-active form of the said compound may be liberated by treatment with acid using a conventional procedure, for example using an aqueous mineral acid such as dilute hydrochloric acid.

The property of inhibiting the enzyme aldose reductase may be demonstrated in the following standard laboratory test. Thus, rats are made diabetic (as evidenced by severe glucosuria being present) by dosing with streptozotocin. The animals are then dosed daily with the test compound for 5 days. The animals are then killed and the eye lenses and sciatic nerves are removed. After a standard work-up procedure the residual sorbitol levels in each tissue are determined by gas liquid chromatography after conversion to the poly-trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

Alternatively, a modified test may be used in which the streptozotocin induced diabetic rats are dosed daily with test compound for two days. After 2-4 hours from the final dose the animals are killed and the sciatic nerves are removed and assessed for residual sorbitol levels as described above.

Preferred compounds in either of these tests reduce residual sorbitol levels to levels which are similar to those of normal, undosed rats. However, in general the compounds of formula I produce significant inhibition of the enzyme aldose reductase at an oral dose of 100 mg/kg or much less. Thus, by way of illustration, 1'-(3,4-dichlorobenzyl)-spiro[imidazolidine-4,3'-indoline]-2,2',5-trione and 1'-(2-fluoro-4-bromobenzyl)-spiro[imidazolidine-4,3'-indoline]-2,2',5-trione both produce a residual sorbitol level in the sciatic nerve which is approximately 20% of that obtained in control undosed diabetic rats, following oral dosing at 10 mg./kg. for 5 days. No overt toxic or other undesirable effects were detected with compounds of formula I at 100 mg./kg. in the above tests.

Preferred compounds of formula I defined hereinbefore in general reduce the residual sorbitol level in the sciatic nerve to that in normal undosed rats when administered at an oral dose in the range 5 to 20 mg./kg.

The property of inhibiting the enzyme aldose reductase may also be demonstrated in vitro. Thus, purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods. In this test the compounds of formula I in general show significant inhibition of the enzyme aldose reductase at a concentration of about $10^{-6}M$ or much less.

When a compound of the invention is used to produce an effect on the enzyme aldose reductase in warm-blooded animals, it may be administered primarily orally at a daily dose of 0.5 to 25 mg./kg., which is equivalent in man to a total daily dose in the range 10 to 750 mg. per man, given in divided doses if necessary.

The compounds of the invention may be administered in the form of pharmaceutical compositions and according to a further feature of the invention there is provided a pharmaceutical composition which comprises a command of formula I, or a pharmaceutically acceptable salt thereof, together with a pharmaceutically acceptable diluent or carrier.

Especially preferred pharmaceutical compositions are those which are in a form suitable for oral administration, for example tablets, capsules, suspensions or solutions, which may be obtained by conventional methods and, if desired, may incorporate conventional diluents, carriers or other excipients. Other preferred compositions are those which are in a form suitable for parenteral administration, for example sterile injectable aqueous or non-aqueous solutions or suspensions, and for rectal administration, for example suppositories. Dosage forms will generally contain from 10 mg. to 250 mg of a compound of formula I, or an equivalent amount of a pharmaceutically acceptable salt thereof, per dosage unit.

The compositions of the invention may also contain one or more other agents which may have a useful effect in the treatment of diabetes or galactosemia, for example a hypoglycaemic agent such as tolbutamide, chlorpropamide, or glybenclamide.

The invention will now be illustrated in the following non-limiting Examples in which, unless otherwise stated:

(i) all evaporations were carried out by rotary evaporation in vacuo (ii) all operations were carried out at room temperature, that is in the range 18°–26° C.;

(iii) petroleum ether (b.p. 60°–80° C.) is referred to as "petrol 60–80", and other petroleum ether fractions accordingly;

(iv) all compounds of formula I were fully characterised on the basis of microanalysis and NMR and IR spectroscopy; and (v) yields (where given) are for illustration and are not necessarily the maximum attainable.

EXAMPLE 1

A mixture of 1-(3,4-dichlorobenzyl)-indoline-2,3-dione (12.0 g), ammonium carbonate (36.0 g.) and potassium cyanide (5.2 g.) in methanol (300 ml.) and water (300 ml.) was heated under reflux at 95°–100° C. for 3 hours. The dark coloured solution obtained was cooled somewhat and decolourising charcoal (3.0 g.) added. The mixture was then heated at 95°–100° C. and all the methanol allowed to distill out. The hot mixture was then separated by filtration and the residue washed with hot water. The filtrate and washings were combined, cooled and acidified with concentrated hydrochloric acid to pH 2. The buf solid which separated was collected, washed with water, air-dried and recrystallized twice from ethyl acetate/petrol 60-80 (4:1 v/v). There was thus obtained 1'-(3,4-dichlorobenzyl)-spiro[imidazolidine-4,3'-indoline]-2,2',5-trione (3.3 g.), m.p. 269°–271° C.

The starting material was obtained as follows:

An ethanol solution of potassium hydroxide (100 ml. of a 1M solution) was added to a stirred solution of indoline-2,3-dione (isatin) (14.7 g.) in dimethyl sulphoxide (200 ml.). After 10 minutes a solution of 3,4-dichlorobenzyl chloride (21.5 g.) in dimethyl sulphoxide (10 ml.) was added. The mixture was stirred for 72 hours, and then poured into water (600 ml.). The solid which formed was collected, washed with water, air-dried and recrystallized from ethyl acetate/petrol 60-80 (3:2 v/v). There was thus obtained 1-(3,4-dichlorobenzyl)-indoline-2,3-dione (13.8 g.), m.p. 183°–184° C.

EXAMPLES 2–5

Using a similar procedure to that described in Example 1, but starting from the appropriate indoline-2,3-dione of formula III, the following compounds of formula I were obtained:

| Example | $R^1$ | Substituent on benzene ring A | m.p. (°C.) | Recrystallisation solvents (v/v) | Yield (%) |
| --- | --- | --- | --- | --- | --- |
| 2 | 2-fluoro-4-bromobenzyl | none | 298–300 | MeOH/EtOAc (1:3) | 19 |
| 3 | naphth-1-ylmethyl | none | 268–270 | i-PrOH/Pet* (1:3) | 25 |
| 4 | n-propyl | 6'-chloro | 261–263 | i-PrOH/Pet* (1:3) | 46 |
| 5 | 3,4-dichlorobenzyl | 5'-fluoro | 240–242 | EtOAc/Pet* (1:3) | 13 |

*petrol 60–80

The necessary starting materials of formula III were obtained in an analogous manner to that described for the starting material in Example I, using the appropriate isatin and halide of the formula $R^1.X$. The following properties and yields were obtained:

| Compound No. | X | $R^1$ | Substituent on benzene ring A | m.p. (°C.) | Recrystallisation solvents (v/v) | Yield (%) |
| --- | --- | --- | --- | --- | --- | --- |
| 1 | Br | 2-fluoro-4-bromobenzyl | none | 151–153 | i-PrOH/Pet* (1:3) | 73 |
| 2 | Cl | naphth-1-ylmethyl | none | 172–174 | EtOAc/Pet* (1:3) | 54 |
| 3 | Br | n-propyl | 6-chloro | 118–120 | Petrol 80–100 | 57 |
| 4 | Cl | 3,4-dichlorobenzyl | 5-fluoro | 190–192 | EtOAc/Pet* (1:3) | 40 |

*petrol 60–80

EXAMPLES 6–33

Using a similar procedure to that described in Example 1, but starting from the appropriate indoline-2,3-dione of formula III, the following compounds of formula I were obtained:

| Example | $R^1$ | Substituent on benzene ring A | m.p. (°C.) | Recrystallisation solvent(s) | + Yield (%) |
| --- | --- | --- | --- | --- | --- |
| 6 | 2,4-Cl$_2$—benzyl | none | 275–277 | i-PrOH/Pet* | 26 |
| 7 | n-nonyl | none | 134–136 | i-PrOH/H$_2$O | 20 |
| 8 | 4-Me—benzyl | none | 260–262 | MeOH | 40 |
| 9 | cinnamyl | none | 250–252 | i-PrOH/Pet | 43 |
| 10 | n-pentyl | none | 181–182 | EtOAc/Pet | 56 |
| 11 | n-hexyl | none | 164–166 | EtOAc/Pet | 60 |
| 12 | n-decyl | none | 156–157 | EtOAc/Pet | 10 |
| 13 | 3,4-Cl$_2$—benzyl | 5'-MeO | 245–247 | EtOAc/Pet | 24 |
| 14 | 3,4-Cl$_2$—benzyl | 5'-Me | 270–272 | Note (a) | 12 |
| 15 | 2F—4I—benzyl | none | 288–289 | MeOH | 32 |
| 16 | 3Cl—4Br—benzyl | none | 272–273 | MeOH | 30 |
| 17 | 3,4-Cl$_2$—benzyl | 5'-Cl | 270–272 | EtOAc/Pet | 21 |
| 18 | 3,4-Cl$_2$—benzyl | 7'-Cl | 239–240 | EtOAc/Pet | 42 |
| 19 | 2F—4Br—benzyl | 5'-Cl | 262–264 | EtOAc/Pet | 18 |
| 20 | 3,4-Cl$_2$—benzyl | 5'-Br | 208–210 | EtOAc/Pet | 7 |
| 21 | 3,4-Cl$_2$—benzyl | 7'-F | 243–244 | EtOAc/Pet | 12 |
| 22 | 4-Br—benzyl | none | 270–271 | DMF/H$_2$O | 8 |
| 23 | 2F—4Br—benzyl | 5'-F | 262–264 | EtOAc/Pet | 15 |
| 24 | 3,4-Cl$_2$—benzyl | 7'-Me | 237–238 | EtOAc/Pet | 18 |
| 25 | 3,4-(MeO)$_2$—benzyl | none | 270–271 | DMF/H$_2$O | 57 |
| 26 | 3-CF$_3$—benzyl | none | 276 | AcOH | 31 |
| 27 | 3,4-Cl$_2$—benzyl | 4'Cl | 264–266 | EtOAc | 8 |
| 28 | 2-CN—benzyl | none | 248–250 | EtOAc/Pet | 47 |
| 29 | naphth-2-ylmethyl | none | 250–252 | i-PrOH/Pet | 20 |
| 30 | benzyl | 5'Br | 250–252 | EtOAc/Pet | 23 |
| 31 | 4-CN—benzyl | none | 282–283 | MeOH | 15 |
| 32 | 3,4-Cl$_2$—cinnamyl | none | 232–233 | EtOAc/Pet | 41 |
| 33 | phenyl | none | 257–259 | EtOAc/Pet | 16 |

*"Pet" stands for "petrol 60–80"
+ Yields are of recrystallised product.
Note (a): purified by column chromatography on silica gel using 1:3 v/v ethyl acetate/toluene as eluant.

The necessary starting materials of formula III were in general obtained in an analogous manner to that described for the starting material in Example 1, starting from the appropriate substituted indoline-2,3-dione and halide of the formula $R^1.X$, and had the following properties:

| Compound No. | X | R¹ | Substituent on benzene ring A | m.p. (°C.) | Recrystallisation solvent(s) | + Yield (%) |
| --- | --- | --- | --- | --- | --- | --- |
| 1 | Cl | 2,4-Cl₂—benzyl | none | 189–190 | EtOAc | 64 |
| 2 | Br | n-nonyl | none | 43–45 | Pet* | 52 |
| 3 | Cl | 4-Me—benzyl | none | 141–143 | EtOAc/Pet | 56 |
| 4 | Br | cinnamyl | none | 137–139 | i-PrOH | 55 |
| 5 | Br | n-pentyl | none | 47–49 | Pet | 27 |
| 6 | Br | n-hexyl | none | 41–42 | Pet | 24 |
| 7 | Br | n-decyl | none | 54–56 | Pet | 38 |
| 8 | Cl | 3,4-Cl₂—benzyl | 5-MeO | 158–159 | Cyclohexane | 22 |
| 9 | Cl | 3,4-Cl₂—benzyl | 5-Me | 199–200 | i-PrOH | 61 |
| 10 | Br | 2F—4I—benzyl | none | 159–160 | MeOH | 28 |
| 11 | Br | 3Cl—4Br—benzyl | none | 188–189 | EtOH | 38 |
| 12 | Cl | 3,4-Cl₂—benzyl | 5-Cl | 171–172 | CCl₄ | 26 |
| 13 | Cl | 3,4-Cl₂—benzyl | 7-Cl | 175–176 | Pet/Toluene | 58 |
| 14 | Cl | 2F—4Br—benzyl | 5-Cl | 164–165 | i-PrOH | 48 |
| 15 | Cl | 3,4-Cl₂—benzyl | 5-Br | 164–166 | i-PrOH | 23 |
| 16 | Cl | 3,4-Cl₂—benzyl | 7-F | Note (a) | — | 77 |
| 17 | Br | 4-Br—benzyl | none | 184–186 | EtOAc | 53 |
| 18 | Br | 2F—4Br—benzyl | 5-F | 167–168 | i-PrOH | 62 |
| 19 | Cl | 3,4-Cl₂—benzyl | 7-Me | 184–186 | i-PrOH | 32 |
| 20 | Cl | 3,4-(MeO)₂—benzyl | none | 125–127 | i-PrOH | 33 |
| 21 | Cl | 3-CF₃—benzyl | none | 160–162 | i-PrOH | 68 |
| 22 | Cl | 3,4-Cl₂—benzyl | 4-Cl | 221–222 | i-PrOH | 53 |
| 23 | Br | 2-CN—benzyl | none | 165–167 | MeOH/i-PrOH | 72 |
| 24 | Br | naphth-2-ylmethyl | none | 174–176 | MeOH/DMF | 59 |
| 25 | Br | benzyl | 5-Br | 150–151 | MeOH/H₂O | 82 |
| 26 | Br | 4-CN—benzyl | none | 222–223 | Acetone | 46 |
| 27 | Cl | 3,4-Cl₂—cinnamyl | none | 194–196 | EtOAc | 55 |

* "Pet" stands for "petrol 60–80"
+ Yields are of recrystallised product.
Note (a) : isolated as a waxy solid, pure by TLC (SiO₂) : 1/1 v/v EtOAc/Toluene).

1-Phenylindoline-2,3-dione (for Example 33) was obtained as a solid, m.p. 138°–139° C. (recrystallised from propan-2-ol) in 56% yield by the procedure of U.S. patent Ser. No. 3,509,149.

EXAMPLE 34

Sulphuryl chloride (16.0 ml.) was added during 10 minutes to a stirred mixture of 1'-(3,4-dichlorobenzyl)-spiro[imidazolidine-4,3'-indoline]-2,2',5-trione (28.2 g.) in acetic acid (400 ml.). The mixture obtained was then stirred at 60°–65° C. for 40 minutes. The clear solution which formed was poured into water (3 l.). The solid which was precipitated was collected by filtration, washed with water and air-dried. Recrystallisation of the crude solid thus obtained from aqueous propan-2-ol gave 1'-(3,4-dichlorobenzyl)-5'-chlorospiro[imidazolidine-4,3'-indoline]-2,2',5-trione (15.4 g.), m.p. 257°–259° C.

EXAMPLES 35–37

Fuming nitric acid (0.2 ml.) was added during 10 minutes to a stirred solution of 1'-(3,4-dichlorobenzyl)-spiro[imidazolidine-4,3'-indoline]-2,2',5-trione (1.79 g.) in concentrated sulphuric acid (1.5 ml.). maintained at a temperature of 0°–5° C. The reaction mixture was then stirred at 0°–5° C. for 1 hour and finally at 5°–20° C. for a further 1 hour. The solution was then poured onto crushed ice (300 g.) and the mixture which formed was extracted with ethyl acetate. The combined extracts were washed with water (3×150 ml.) then with brine (100 ml.) and dried (MgSO₄). The extracts were evaporated and the residual oil was redissolved in ethyl acetate (20 ml.). The solution was evaporated on to chromatographic silica gel and the solid residue added to the top of a column of the same silica gel made up in toluene. The column was eluted with increasing concentrations of ethyl acetate in toluene (up to 1:1 v/v). The fractions containing the major component [TLC: Rf~0.6 on SiO₂: eluant 1:1 v/v EtOAc/toluene] were combined and evaporated. The residue was recrystallised from a mixture of toluene, ethyl acetate and petrol 60–80 to give 1'-(3,4-dichlorobenzyl)-5'-nitrospiro[imidazolidine-4,3'-indoline]-2,2',5-trione (Example 35) (0.46 g.), m.p. 249°–251° C.

Using a similar procedure, but starting from 1'-(2-fluoro-4-bromobenzyl)spiro[imidazolidine-4,3'-indoline]-2,2',5-trione and 1'-benzyl-5'-bromospiro[imidazolidine-4,3'-indoline]-2,2',5-trione respectively there were obtained: 1'-(2-fluoro-4-bromobenzyl)-5'-nitrospiro[imidazolidine-4,3'-indoline]-2,2',5-trione (Example 36), m.p. 180°–181° C. (recrystallised from i-PrOH/petrol 60–80) in 36% yield; and 1'-(4-nitrobenzyl)-5'-bromo-7'-nitrospiro[imidazolidine-4,3'-indoline] 2,2',5-trione (Example 37), m.p. 245°–246° C. (recrystallised from EtOAc/petrol 60–80) in 7% yield.

EXAMPLES 38–41

Trimethylsilyl cyanide (0.6 g.) was added to a stirred solution of 1-(4-bromo-3,5-dichlorobenzyl)indoline-2,3-dione (1.2 g.) in dry 1,2-dimethoxyethane (40 ml.). The mixture was stirred for 5 hours to give 1-(4-bromo-3,5-dichlorobenzyl)-3-cyano-3-(trimethylsilyloxy)-indoline-2-one in situ. A solution of ammonium carbonate (6.0 g.) in water (40 ml.) was then added. The subsequent mixture was heated under reflux for 6 hours, cooled and evaporated. The residue was treated with water (100 ml.) and the mixture separated by filtration. The residue was washed with warm water (2×50 ml.). The aqueous filtrate and washings were cooled to 0°–5° C. and acidified to pH4 with 2M hydrochloric acid. The solid which separated was collected by filtration, washed with water, air-dried and recrystallized from aqueous N,N-dimethylformamide (DMF) (1:1 v/v) to give 1'-(4-bromo-3,5-dichlorobenzyl)spiro[imidazolidine-4,3'-indoline]-2,2',5-trione (Example 38) (0.63 g.), m.p. 290°–292° C.

Using a similar procedure, but starting from the appropriate 1-benzyl-indoline-2,3-dione there were obtained the following compounds:

(Example 40): 1'-(3,4-dichlorobenzyl)-5',6'-dimethyl-spiro[imidazolidine-4,3'-indoline]-2,2',5-trione, m.p. 262°–263° C. (recrystallised from EtOAc/petrol 60-80) in 10% yield; and (Example 41): 1'-(3,4-dichlorobenzyl)-7'-ethyl-spiro[imidazolidine-4,3'-indoline]-2,2',5-trione, m.p. 232°–233° C. (recrystallised from EtOAc/petrol 60-80) in 7% yield.

The necessary starting materials of formula III were obtained using a similar procedure to that described for the analogous starting material in Example I starting from the appropriate indoline-2,3-dione and halide of the formula $R^1X$ and had the following properties:

| Compound No. | X | $R^1$ | Substituent(s) on benzene ring A | m.p. (°C.) | Recrystallisation solvent(s) | Yield (%) |
| --- | --- | --- | --- | --- | --- | --- |
| 1 | Cl | 4-Br—3,5-Cl$_2$—benzyl | none | 241–243 | MeOH | 34 |
| 2 | Cl | 3,4-Cl$_2$—benzyl | 6-Cl | 180–182 | i-PrOH | 25 |
| 3 | Cl | 3,4-Cl$_2$—benzyl | 5,6-Me$_2$ | 218–220 | EtOAc | 31 |
| 4 | Cl | 3,4-Cl$_2$—benzyl | 7-Et | 124–126 | petrol 60–80 | 12 |

EXAMPLES 42–48

Using a similar procedure to that described in Example 1, but starting from the appropriate 1-substituted indoline-2,3-dione of formula III, the following compounds of formula I were obtained:

| Example | $R^1$ | Substituent(s) on benzene ring A | m.p. (°C.) | Recrystallisation Solvents | +Yield (%) |
| --- | --- | --- | --- | --- | --- |
| 42 | 4-Me—benzyl | 5'-Cl | 257–259 | EtOAc/pet* | 12 |
| 43 | methyl | 5'-Cl | 306–308 | Acetone/pet* | 25 |
| 44 | n-hexyl | 5'-Cl | 158–160 | EtOAc/pet* | 26 |
| 45 | 3,4-Cl$_2$—benzyl | 4',5'-Cl$_2$ | 155–156 (decomp) | EtOAc/pet* | 10 |
| 46 | 3,4-(MeO)$_2$—benzyl | 5'-Cl | 285–287 | EtOAc/pet* | 14 |
| 47 | 3,4-Cl$_2$—benzyl | 5'-Cl—7'-Me | 273–275 | EtOH/2-MeO—EtOH | 29 |
| 48 | 2-F—4-Br—benzyl | 5'-Cl—7'-Me | 247–249 | EtOAc/pet* | 25 |

+ - Yields are of recrystallised material
*"Pet" stands for "Petrol 60–80"

(Example 39): 1'-(3,4-dichlorobenzyl)-6'-chloros-piro[imidazolidine-4,3'-indoline]-2,2',5-trione, m.p. 286°–287° C. (recrystallised from EtOAc/petrol 60-80) in 57% yield.

The necessary starting materials of formula III were obtained in an analogous manner to that described for the starting material in Example 1 that is by reaction of the appropriate indoline-2,3-dione with a halide of the formula $R^1.X$, and had the following properties:

| Compound No. | X | $R^1$ | Substituent(s) on benzene ring A | m.p. (°C.) | Recrystallisation Solvent(s) | +Yield (%) |
| --- | --- | --- | --- | --- | --- | --- |
| 1 | Br | 4-Me—benzyl | 5-Cl | 156–158 | i-PrOH | 52 |
| 2 | I | methyl | 5-Cl | 170–172 | i-PrOH | 60 |
| 3 | Br | n-hexyl | 5-Cl | 86–88 | i-PrOH | 49 |
| 4 | Cl | 3,4-Cl$_2$—benzyl | 4,5-Cl$_2$ | 185–187 | EtOAc/pet* | 71 |
| 5 | Cl | 3,4-(MeO)$_2$—benzyl | 5-Cl | 162–164 | i-PrOH/DMF | 33 |
| 6 | Cl | 3,4-Cl$_2$—benzyl | 5-Cl—7-Me | 191–194 | MeCN/2-MeO—EtOH | 41 |
| 7 | Cl | 2-F—4-Br—benzyl | 5-Cl—7-Me | 179–182 | MeCN/2-MeO—EtOH | 43 |

+ - Yields are of recrystallised material
*"pet" stands for "petrol 60–80"

EXAMPLES 49–53

Using a similar procedure to that described in Example 38, but starting from the appropriate 1-benzylindoline-2,3-dione of formula III and with intermediate formation of the corresponding 1-benzyl-3-trimethylsilyloxy-3-cyano-indoline-2-one of the formula VII ($R^3$=trimethylsilyl), the following compounds of formula I may be obtained:

| Example | $R^1$ | Substituent(s) on benzene ring A | m.p. (°C.) | Recrystallisation Solvent(s) | + Yield (%) |
|---|---|---|---|---|---|
| 49 | 3,4-$Cl_2$—cinnamyl | 5'-Cl | 295–297 | DMF/$H_2O$ | 16 |
| 50 | 4-HO—benzyl | none | 285–286 | MeOH | 52 |
| 51 | 3,4-$Cl_2$—benzyl | 5',6'-$F_2$ | 244–245 | EtOAc/petrol 80–100 | 11 |
| 52 | 3,4-$Cl_2$—benzyl | 5',6'-$Cl_2$ | 255–256 | EtOAc/petrol 60–80 | 8 |
| 53 | 3,5-$Cl_2$— | none | 237–238 | Toluene | 54 |

+ - Yields are of recrystallised material.

The necessary starting materials of formula III were in general obtained in an analogous manner to that described for the starting material in Example 1 that is by reaction of the appropriate indoline-2,3-dione with a halide of the formula $R^1.X$, and had the following properties:

| Compound No | X | $R^1$ | Substituent(s) on benzene ring A | m.p. (°C.) | Recrystallisation solvent(s) | + Yield (%) |
|---|---|---|---|---|---|---|
| 1 | Cl | 3,4-$Cl_2$—cinnamyl | 5-Cl | 194–196 | EtOAc | 55 |
| 2 | Cl | 3,4-$Cl_2$—benzyl | 5,6-$F_2$ | 170–171 | Toluene | 5 |
| 3 | Cl | 3,4-$Cl_2$—benzyl | 5,6-$Cl_2$ | 197–200 | EtOAc/pet* | 70 |
| 4 | Cl | 3,5-$Cl_2$—benzyl | none | 192–193 | EtOH | 48 |

+ - Yields are of recrystallised material.
*"pet" stands for "petrol 60–80"

The compound 1-(4-hydroxybenzyl)-indoline-2,3-dione required as starting material for Example 50 was obtained as follows:

An ethanol solution of potassium hydroxide (16.6 g. in 400 ml.) was added to a stirred solution of indoline-2,3-dione (isatin) (43.6 g.) in dimethylsulphoxide (400 ml.). After 10 minutes a solution of 4-acetoxybenzyl bromide (76.3 g.) in dimethylsulphoxide (40 ml.) was added. The mixture was stirred for 72 hours and then poured into ice/water (~1000 ml.). The gum which first formed slowly crystallised. The solid which formed was recrystallised from methanol (500 ml.) to give 1-(4-acetoxybenzyl)indoline-2,3-dione as a solid, m.p. 159°–161° C.

This solid, together with further material obtained from the mother liquors, was chromatographed on silica (500 g.) using toluene containing an increasing amount of ethyl acetate as eluant (up to 25% v/v). The fractions of eluate collected using eluant containing 20–25% v/v ethyl acetate were combined and evaporated to give 1-(4-hydroxybenzyl)-indoline-2,3-dione as a low melting solid (m.p. 28°–35° C.) after recrystallisation from a mixture of toluene and ethyl acetate.

Note: It will be appreciated that the acetoxy group is hydrolysed to the required hydroxy group during the above chromatography on silica.

EXAMPLE 54

A mixture of pyridine (20 ml.) and concentrated hydrochloric acid (20 ml.) was heated at about 180° C. for 20 minutes. 1'-(3,4-Dichlorobenzyl)-5'-methoxyspiro[imidazolidine-4,3'-indoline]-2,2',5-trione (2.0 g.) was then added and the subsequent mixture was further heated for 1 hour at about 180° C. The solution obtained was cooled and poured into water (200 ml.). The aqueous mixture was extracted with ethyl acetate (2×200 ml.). The combined extracts were washed with water (3×100 ml.), then with brine (saturated sodium chloride solution) (100 ml.), dried (MgSO4) and evaporated. The resultant oil was dissolved in ethyl acetate (20 ml.) and evaporated onto chromatographic silica gel (10 g.), which was then added to the top of a column of the same silica gel (100 g.) made up in toluene. The column was then eluted with toluene containing an increasing concentration of ethyl acetate (up to 50% v/v). The fractions of eluate collected using eluant containing 50% v/v ethyl acetate were combined and evaporated to give 1'-(3,4-dichlorobenzyl)-5'-hydroxyspiro[imidazolidine-4,3'-indoline]-2,2',5-trione (0.7 g.), m.p. 296°–298° C. (after recrystallisation from ethyl acetate/petrol 60–80).

EXAMPLE 55

A filtered solution of 1'-(3,4-dichlorobenzyl)-spiro[imidazolidine-4,3'-indoline]-2,2',5-trione (3.76 g.) in water (20 ml.) containing sodium hydroxide (0.40 g.) was evaporated, remaining traces of water being removed by azeotropic distillation with toluene. There was thus obtained the corresponding mono-sodium salt in quantitative yield as an amorphous hygroscopic solid having a satisfactory microanalysis.

EXAMPLE 56

Sodium hydride (1.5 g., 50% w/w dispersion in mineral oil) was added continuously to a solution of spiro[imidazoline-4,3'-indoline]-2,2',5-trione (2.17 g.) in N,N-dimethylformamide (40 ml.) and water (20 ml.).

The resultant mixture was stirred for 30 minutes and then a solution of 3,4-dichlorobenzyl chloride (1.95 g.) in tetrahydrofuran (5 ml.) was added dropwise during 10 minutes. The solution obtained was stirred at room temperature for two hours and then poured into water (150 ml.). The mixture was acidified with concentrated hydrochloric acid and then extracted with ether (2×100 ml.). The combined extracts were washed with water (3×100 ml.), then with saturated sodium chloride solution (100 ml.), dried (MgSO₄) and evaporated. The residual solid was dissolved in chloroform and purified by chromatography on silica (25 g.) using an increasing concentration of ethyl acetate in cyclohexane as eluant. Evaporation of the ethyl acetate rich fractions gave 1'-(3,4-dichlorobenzyl)-spiro[imidazolidine-4,3'-indoline]-2,2',5-trione identical with that obtained in Example 1.

EXAMPLE 57 (all parts by weight

A mixture of 1'-(3,4-dichlorobenzyl)-spiro[imidazolidine-4,3'-indoline]-2,2',5-trione (50 parts), lactose (27 parts) and maize starch (20 parts), was stirred thoroughly and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 and 100 mg. of active ingredient and suitable for oral administration for therapeutic purposes.

Using a similar procedure, but replacing the active ingredient by any other compound of the invention or a salt thereof, for example as described in any one of the aforegoing Examples, tablets containing 10, 20, 50 and 100 mg. of active ingredient may be obtained.

EXAMPLE 58

(dl)-1'-(3,4-Dichlorobenzyl)-spiro[imidazolidine-4,3'-indoline]-2,2'-5-trione (4.4 g.) was added to 61.5 ml of a 0.19M solution of (l)-N,N,N-trimethyl(1-phenylethyl)ammonium hydroxide. The mixture was warmed to facilitate solution and then evaporated. The residue was dissolved in warm propan-2-ol (11 ml.). The solution obtained was cooled to 0° C. for 48 hours. The crystalline solid which formed was collected by filtration, washed with cold propan-2-ol (5 ml.), then with petrol 40-60 (20 ml.) and recrystallised twice from propan-2-ol to give the (d)-diastereoisomeric salt of (l)-N,N,N-trimethyl(1-phenylethyl)ammonium hydroxide and (d)-1'-(3,4-dichlorobenzyl)-spiro[imidazolidine-4,3'-indoline]-2,2',5-trione (1.6 g.), m.p. 148°-150° C., [α]$_D^{23}$+32.8° (c, 1.4; MeOH).

The salt (1.6 g.) was dissolved in water (10 ml.) and methanol (3 ml.) and the solution acidified with concentrated hydrochloric acid (1 ml.). The precipitated solid was collected, washed with water and recrystallised from ethanol to give (d)-1'-(3,4-dichlorobenzyl)-spiro[imidazolidine-4,3'-indoline]-2,2',5-trione, m.p. 199°-200° C., [α]$_D^{23}$+41° (c, 1.6, MeOH).

The starting quaternary ammonium hydroxide solution was obtained by passing an aqueous solution (l)-N,N,N-trimethyl(1-phenylethyl)ammonium iodide (27.8 g.) (I. Angres and H. E. Zieger, *J. Org. Chem.* 1975, 40, 1457–1460) down a column of anion exchanging resin ('Amberlite' IRA 401, 200 g.) newly converted into the hydroxide form. ('Amberlite' is a trademark).

It will be appreciated that other single enantiomers of optically active quaternary ammonium hydroxides, for example of N,N,N-trimethyl-(1-methyl-2-hydroxy-2-phenylethyl)ammonium hydroxide, may also be used to resolve racemic forms of compounds of formula I.

What is claimed is:

1. A 1'-substituted-spiro[imidazolidine-4,3'-indoline]-2,2',5-trione of the formula:

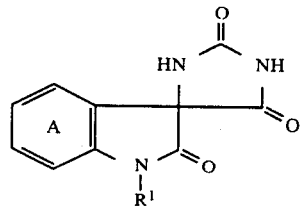

wherein:
(a) R¹ is a (1–12C) alkyl or benzyl radical; and benzene ring A bears one or two halogeno radicals;
(b) R¹ is a phenyl, cinnamyl or naphthylmethyl radical the aromatic rings of which optionally bear one or two halogeno radicals; and benzene ring A is unsubstituted or bears one or two halogeno substituents; or
(c) R¹ is a benzyl radical bearing 1-3 substituents independently selected from halogeno, trifluoromethyl, cyano, hydroxy, nitro, methyl and methoxy radicals; and benzene ring A optionally bears one substituent selected from the group consisting of halogeno, (1–4C) alkyl, (1–4C) alkoxy, nitro and hydroxy radicals, or bears two substituents independently selected from the group consisting of halogeno, (1–4C) alkyl and nitro radicals; or a pharmaceutically acceptable salt thereof.

2. A compound as claimed in claim 1 wherein R¹ is a methyl, ethyl, propyl, butyl, pentyl, hexyl, nonyl or decyl radical, a phenyl, naphthylmethyl or cinnamyl radical, the aromatic rings of which optionally bear one or two fluoro, bromo or iodo radicals; or a benzyl radical; and benzene ring A bears at least one fluoro, chloro, bromo or iodo radical; or R¹ is a benzyl radical bearing one, two or three substituents independently selected from fluoro, chloro, bromo, iodo, trifluoromethyl, methyl, ethyl, methoxy, ethoxy, nitro, cyano and hydroxy radicals; and benzene ring A optionally bears one substituent selected from the group consisting of fluoro, chloro, bromo, iodo, methyl, ethyl, methoxy, ethoxy, nitro and hydroxy radicals, or bears two substituents independently selected from the group consisting of fluoro, chloro, bromo, iodo, methyl, ethyl and nitro radicals; or a pharmaceutically acceptable salt thereof.

3. A compound as claimed in claim 1 wherein R¹ is a methyl, ethyl, n-propyl, n-hexyl, n-nonyl, n-decyl, phenyl, cinnamyl, 3,4-dichlorocinnamyl, naphth-1-ylmethyl, naphth-2-ylmethyl or benzyl radical; and benzene ring A bears substituents selected from the group consisting of 4'-chloro, 5'-fluoro, 5'-chloro, 5'-bromo, 6'-chloro, 7'-fluoro, 7'-chloro, 5',6'-difluoro, 5',6'-dichloro and 4',5'-dichloro substituents; or R¹ is a 3,4-dichlorobenzyl, 2-fluoro-4-bromobenzyl, 4-methylbenzyl, 2-fluoro-4-iodobenzyl, 3-chloro-4-bromobenzyl, 4-chlorobenzyl, 4-bromobenzyl, 3,4-dimethoxybenzyl, 3-(trifluoromethyl)-benzyl, 2-cyanobenzyl, 4-cyanobenzyl, 2-fluoro-4-bromo-5-nitrobenzyl, 4-nitrobenzyl, 3,5-dichloro-4-bromobenzyl, 2,3-dichlorobenzyl, 4- hydroxybenzyl or 3,5-dichlorobenzyl radical; and benzene ring A is unsubstituted or bears substituents selected from the group consisting of 4'-chloro, 5'-fluoro, 5'-chloro, 5'-bromo, 5'-methyl, 5'-methoxy, 5'-hydroxy, 5'-nitro, 6'-chloro, 7'-fluoro, 7'-chloro, 7'-methyl, 7'-ethyl, 5',6'-difluoro, 5',6'-dichloro, 4',5'-dichloro, 5',6'-dimethyl, 5'-bromo-7'-nitro and 5'-chloro-7'-methyl substituents.

4. A compound as claimed in claim 1 wherein $R^1$ is a 4-halogeno-, 2,4-dihalogeno-, 3,4-dihalogeno or 3,5-dihalogeno-benzyl radical in which the halogeno substituent may be the same or different, and benzene ring A is unsubstituted or bears a halogeno substituent located at position 5',6' or 7'.

5. A 1'-substituted-spiro[imidazolidine-4,3'-indoline]-2,2',5-trione of the formula I set out in claim 1 wherein $R^1$ is a 3,4-dichlorobenzyl, 2-fluoro-4-bromobenzyl, 3-chloro-4-bromobenzyl or 2-fluoro-4-iodobenzyl radical and benzene ring A is unsubstituted or bears 5'-fluoro, 5'-chloro, 5'-bromo, 5',6'-difluoro or 5',6'-dichloro substituents; or a pharmaceutically acceptable salt thereof.

6. A 1'-substituted-spiro[imidazolidine-4,3'-indoline]-2,2',5-trione selected from the group consisting of:
1'-(3,4-dichlorobenzyl)-spiro[imidazolidine-4,3'-indoline]-2,2',5-trione.
1'-(2-fluoro-4-bromobenzyl)-spiro[imidazolidine-4,3'-indoline]-2,2',5-trione.
1'-(3,4-dichlorobenzyl)-5'-fluorospiro[imidazolidine-4,3'-indoline]-2,2', 5-trione,
1'-(3-chloro-4-bromobenzyl)-spiro[imidazolidine-4,3'-indoline]-2,2'-5-trione,
1'-(3,4-dichlorobenzyl)-5'-chlorospiro[imidazolidine-4,3'-indoline]-2,2',5-trione,
1'-(2-fluoro-4-bromobenzyl)-5'-chlorospiro[imidazolidine-4,3'-indoline]-2,2',5-trione,
1'-(3,4-dichlorobenzyl)-5'-bromospiro[imidazolidine-4,3'-indoline]-2,2',5-trione,
1'-(2-fluoro-4-bromobenzyl)-5'-fluorospiro[imidazolidine-4,3'-indoline]-2,2',5-trione,
1'-(3,4-dichlorobenzyl)-5',6'-dichlorospiro[imidazolidine-4,3'-indoline]-2,2',5-trione,
1'-(3,4-dichlorobenzyl)-5',6'-difluorospiro[imidazolidine-4,3'-indoline]-2,2',5-trione and
1'-(2-fluoro-4-iodobenzyl)-spiro[imidazolidine-4,3'-indoline]-2,2',5-trione; or a pharmaceutically acceptable salt thereof.

7. A pharmaceutically acceptable salt of a compound of formula I as claimed in claim 1 which is selected from the group consisting of alkali metal, alkaline earth metal, aluminium and ammonium salts, or a salt with an organic base forming a pharmaceutically acceptable cation.

8. A pharmaceutical composition suitable for use in inhibiting the enzyme aldose reductase which comprises a therapeutically effective amount of a 1'-substituted-spiro[imidazolidine-4,3'-indoline]-2,2',5-trione of the formula

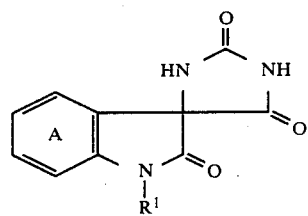

wherein $R^1$ is a (1–12C)alkyl radical, a phenyl, naphthylmethyl or cinnamyl radical the aromatic rings of which optionally bear one or two halogeno radicals, or $R^1$ is a benzyl radical optionally bearing one, two or three substituents independently selected from the group consisting of halogeno, trifluoromethyl, (1–4C)alkyl, (1–4C)alkoxy, nitro, cyano and hydroxy radicals; and benzene ring A optionally bears one substituent selected from the group consisting of halogeno, (1–4C)alkyl, (1–4C)alkoxy, nitro and hydroxy radicals, or bears two substituents independently selected from the group consisting of halogeno, (1–4C)alkyl and nitro radicals; or a pharmaceutically acceptable salt thereof; but excluding those compounds wherein $R^1$ is a methyl, ethyl, n-propyl or unsubstituted benzyl radical, and benzene ring A is unsubstituted, together with a pharmaceutically acceptable diluent or carrier.

9. A method for inhibiting the enzyme aldose reductase in an animal requiring such treatment which comprises administering to said animal an effective amount of a 1'-substituted-spiro[imidazolidine-4,3'-indoline]-2,2',5-trione of the formula

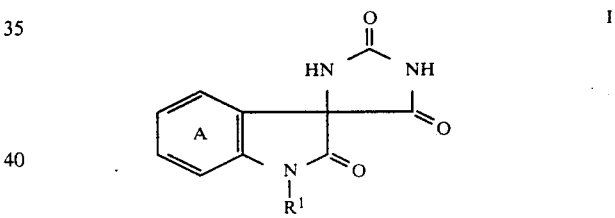

wherein $R^1$ is a (1–12C)alkyl radical, a phenyl, naphthylmethyl or cinnamyl radical the aromatic rings of which optionally bear one or two halogeno radicals, or $R^1$ is a benzyl radical optionally bearing one, two or three substituents independently selected from the group consisting of halogeno, trifluoromethyl, (1–4C)alkyl, (1–4C)alkoxy, nitro, cyano and hydroxy radicals; and benzene ring A optionally bears one substituent selected from the group consisting of halogeno, (1–4C)alkyl, (1–4C)alkoxy, nitro and hydroxy radicals, or bears two substituents independently selected from the group consisting of halogeno, (1–4C)alkyl and nitro radicals; or a pharmaceutically acceptable salt thereof; but excluding those compounds wherein $R^1$ is a methyl, ethyl, n-propyl or unsubstituted benzyl radical, and benzene ring A is unsubstituted.

* * * * *